United States Patent [19]

Yamamoto et al.

[11] 4,139,562

[45] Feb. 13, 1979

[54] PROCESS FOR PURIFYING CRUDE p-AMINOPHENOL

[75] Inventors: Ryuichi Yamamoto; Yutaka Hirai; Teruyuki Nagata, all of Omuta, Japan

[73] Assignee: Mitsui Toatsu Chemicals, Inc., Tokyo, Japan

[21] Appl. No.: 886,129

[22] Filed: Mar. 13, 1978

[51] Int. Cl.$^2$ .................................................. C07C 85/26
[52] U.S. Cl. ...................................... 260/575; 260/705
[58] Field of Search .................................. 260/575, 582

[56] References Cited

U.S. PATENT DOCUMENTS

| | | | |
|---|---|---|---|
| 2,446,519 | 8/1948 | Bean | 260/575 |
| 2,464,194 | 3/1949 | Zimmerman | 270/575 |
| 3,177,256 | 4/1965 | Holtzclaw et al. | 260/575 |
| 3,301,904 | 1/1967 | Cryer | 260/582 |
| 3,694,508 | 9/1972 | Baron et al. | 260/575 |
| 3,703,598 | 11/1972 | Baron | 260/575 |
| 3,717,680 | 2/1973 | Baron et al. | 260/575 |

FOREIGN PATENT DOCUMENTS

| | | | |
|---|---|---|---|
| 37-11104 | 8/1962 | Japan | 260/582 |
| 1228568 | 4/1971 | United Kingdom | 260/575 |
| 282329 | 4/1969 | U.S.S.R. | 260/582 |

Primary Examiner—Winston A. Douglas
Assistant Examiner—John Doll
Attorney, Agent, or Firm—Cushman, Darby & Cushman

[57] ABSTRACT

A process for purifying crude p-aminophenol which contains 4,4'-diaminodiphenyl ether and other impurities, which process comprising adding an alkali metal compound to the crude p-aminophenol in an aqueous medium in an atmosphere of an inert gas and, if necessary, in the presence of a reducing agent to give an aqueous solution of an alkali metal salt of p-aminophenol, and contacting the aqueous solution with an inert organic solvent immiscible with water to permit 4,4'-diaminodiphenyl ether and other impurities to be separated by extraction in the solvent.

10 Claims, No Drawings

PROCESS FOR PURIFYING CRUDE P-AMINOPHENOL

BACKGROUND OF THE INVENTION

1. Field of the Invention

This invention relates to a process for purifying crude p-aminophenol which is particularly suitable for removing 4,4'-diaminodiphenyl ether from the crude p-aminophenol. In a specific aspect, the present invention is concerned with a process for purifying crude p-aminophenol obtained by catalytic reduction of nitrobenzene in an aqueous sulfuric acid medium. The pure p-aminophenol obtained according to the process of the invention is useful as a starting material for medicines.

2. The Prior Art

As well known, p-aminophenol has been used from old as an intermediate for an antioxidant of dyes or a photographic developer. In recent years, since aminopyrine or phenacetin (i.e., acetophenetidine) generally used as an antipyretic and anodyne is encountered with a problem of side effect, there has been a rapidly growing demand for harmless p-N-acetylaminophenol. Thus, p-aminophenol becomes important as an intermediate for p-N-acetylaminophenol.

Para-aminophenol has been heretofore produced from p-nitrobenzene. In recent years, a process of catalytically reducing nitrobenzene in an aqueous sulfuric acid medium has been newly developed and has been reduced into practice on an industrial scale. Para-aminophenol obtained by the catalytic reduction of nitrobenzene generally contains aniline, 4,4'-diaminodiphenyl ether (hereinlater referred to simply as DADPE) and other by-products as described in French Pat. No. 1,564,882. Removal of these impurities will be necessary depending on the purpose for which the aminophenol is intended to apply. However, the removal of such impurities are difficult.

For instance, French Pat. Nos. 1,564,882 and 2,029,142 describe that the crude p-aminophenol obtained by the catalytic reduction of nitrobenzene in aqueous sulfuric acid medium is contacted with aliphatic, alicyclic or aromatic ketones including acetone to remove the impurities from the p-aminophenol by extraction. In British Pat. No. 1,028,078, there is described a method in which the crude p-aminophenol is washed with an aliphatic alcohol to remove the impurities therefrom. However, the solvents of the type indicated above dissolve p-aminophenol as well as the impurities, so that complete removal of the impurities results in a relatively great loss of p-aminophenol.

Japanese Patent Laid-open No. 46-411 describes an improved process which comprises contacting p-aminophenol in aqueous acid medium in a specific pH range of 4.8-5.8 with an aprotic solvent such as methylene dichloride which is immiscible with water and can selectively dissolve the impurities such as DADPE, thereby removing the impurities by extraction. However, this process is also disadvantageous in that the solubility of the impurities, particularly DADPE, in such solvent is very small as stated in the specification, so that complete removal of the impurities requires large amount of the solvent and repetitions of extraction. Even though there is used such solvent as to selectively dissolve DADPE and other impurities, use of such solvent in large amount will result in a loss of p-aminophenol in appreciable amount. In addition, the repetitions of extraction is inconvenient in an industrial sense.

SUMMARY OF THE INVENTION

It is accordingly an object of the present invention to provide a process for preparing highly pure p-aminophenol which is free of DADPE and other impurities.

It is another object of the present invention to provide a process for preparing pure p-aminophenol by which DADPE and other impurities are efficiently removable by extraction without involving any change in quality and any dissolution in solvent of p-aminophenol.

It is a further object of the present invention to provide a process for preparing pure p-aminophenol which is useful as an intermediate for the medical purpose.

According to the present invention, there is provided a process for preparing highly pure p-aminophenol which comprises adding in an aqueous medium an alkali metal compound to crude p-aminophenol containing DADPE and other impurities in an atmosphere of an inert gas to give an aqueous solution of an alkali metal salt of p-aminophenol, and contacting the aqueous solution with an inert organic solvent immiscible with water to permit the impurities to be selectively removed by extraction. By the process, highly pure p-aminophenol which is useful as an intermediate for medicines can be efficiently obtained without change in quality and dissolution in solvent.

According to one aspect of the present invention, the crude p-aminophenol obtained by catalytically reducing nitrobenzene in an aqueous sulfuric acid medium is added with an alkali in an atmosphere of an inert gas and in the presence of a reducing agent to adjust its pH to 7-8 and the resulting precipitate of crude p-aminophenol is separated from the liquid phase. Then, the separated p-aminophenol is re-dissolved in an aqueous alkali metal solution to form an aqueous solution of an alkali metal salt of crude p-aminophenol. The aqueous solution is then contacted with an inert organic solvent immiscible with water to permit the impurities present in the system to be selectively extracted in the organic solvent.

In the above process, DADPE is removable from p-aminophenol to such an extent that little or no DADPE is detectable by a gas-chromatography using a silicone-base filler, which is known as an analytical method for DADPE. The purity of p-aminophenol readily reaches a level as high as 99.3% or more.

DESCRIPTION OF THE PREFERRED EMBODIMENTS

We have made an extensive study of improvements in purification of crude p-aminophenol containing DADPE and other impurities. As a result, it has been found that an aqueous solution of an alkali metal salt of crude p-aminophenol is stable in an atmosphere of an inert gas, for example, nitrogen gas, and, preferably, in the presence of small amount of a reducing agent such as anhydrous sodium dithionite, contrary to an apprehension that such salt is susceptible to oxidation. The process of the present invention is now feasible on the basis of a fact that when the aqueous solution of an alkali metal salt of p-aminophenol is contacted with water-immiscible organic solvent, DADPE and other impurities inherently contained in crude p-aminophenol are readily extracted in the solvent.

According to one embodiment of the present invention, crude p-aminophenol in the form of crystals is added to an aqueous solution of an alkali metal compound in an atmosphere of an inert gas to form an aqueous solution of the alkali metal salt and then the solution is contacted with a water-immiscible inert organic solvent.

According to another embodiment of the present invention which is favorable to industrial application, an aqueous sulfuric acid solution of p-aminophenol obtained by catalytically reducing nitrobenzene in an aqueous sulfuric acid medium is added with an alkali metal compound and then contacted with the solvent for extraction of the impurities.

According to a further embodiment which is more preferable for industrial application, the aqueous sulfuric acid solution of p-aminophenol is first added with an alkali, preferably aqueous ammonia, to adjust its pH to 7–8 thereby precipitating crude p-aminophenol as crystals. The crystals are separated from the solution and then dissolved in an aqueous solution of an alkali metal compound to give an aqueous solution of the alkali metal salt of p-aminophenol, followed by contacting with the solvent.

In those embodiments, any alkali metals may be used for the formation of the aqueous solution of an alkali metal salt of p-aminophenol. Preferably, sodium or potassium is used generally in the form of a hydroxide. The amount of the alkali metal is preferably in the range of one mole or more, most preferably in the range of 1.0 to 1.3 moles, per mole of p-aminophenol. When the alkali metal is used in such a range as defined above, the aqueous alkali metal salt solution is controlled to have a pH value of 12–13.

In the preparation of the aqueous solution of an alkali metal salt of crude p-aminophenol, the concentration of p-aminophenol is preferred to be in the range of 10–25 wt %, and the concentration of the alkali metal compound is preferably in the range of 5–15 wt %. The alkali metal compound is used in an amount sufficient to completely dissolve crude p-aminophenol, i.e., when, for example, an alkali is added to an aqueous sulfuric acid solution of crude p-aminiphenol to precipitate crude p-aminophenol under pH conditions of 7–8 and the thus precipitated crystals are dissolved in an aqueous solution of an alkali metal compound, the alkali metal compound is used in an amount sufficient to completely dissolve the p-aminophenol.

The preparation of an aqueous alkali metal salt by dissolving crude p-aminophenol in an aqueous solution of an alkali metal compound is conducted in a temperature range, preferably, up to 30° C., in an atmosphere of an inert gas, preferably nitrogen gas, and preferably, in the presence of a reducing agent such as anhydrous sodium dithionite or sodium sulfite. The inert gas is filled to prevent the aqueous solution of the alkali metal salt of crude p-aminophenol from contacting with air or oxidative atmosphere. The reducing agent is employed in an amount of 0.01–1.0 wt % of the aqueous solution.

The inert organic solvent which is used to extract and remove DADPE and other impurities by contact with the aqueous alkali metal salt solution should be immiscible with water. In this connection, the inert organic solvent is not necessarily required to have an absolute immiscibility with water, e.g., the miscibility of the solvent will suffice to be a level corresponding to or less than a miscibility of aniline with water. Usable inert organic solvents are those which are immiscible with water and capable of dissolving DADPE satisfactorily and which are liquid at operating temperatures. Examples of the solvent include aromatic amines such as aniline, toluidine, xylidine and a mixture thereof and aliphatic and alicyclic ketones such as methyl isobutyl ketone, methyl-n-amyl ketone, ethyl-n-butyl ketone, cyclohexanone, o-methylcyclohexanone and the like. These solvents have relatively high solubility of DADPE and other impurities. Of these, aniline is preferred because it is relatively inexpensive and is capable of dissolving DADPE.

The extraction of DADPE and other impurities is feasible either batch-wise or in continuous manner. The extracting operation is conducted generally in the range of room temperature to a boiling point of solvent, preferably room temperature to 70° C.

The amount of the solvent used on extraction may vary depending on the manner of extraction but is generally in the range of 0.1 to 0.5 times that of the aqueous solution of alkali metal salt. If necessary, the extraction with the inert organic solvent may be repeated.

The aqueous solution of an alkali metal salt of p-aminophenol from which DADPE and other impurities have been removed by extraction with the inert organic solvent is then added with a mineral acid such as sulfuric acid, hydrochloric acid or the like to adjust its pH to 7–8, preferably about 7.2 to permit precipitation of pure p-aminophenol. The precipitated p-aminophenol is separated and dried to obtain pure p-aminophenol.

In the practice of the invention, the preparation of the aqueous solution of an alkali metal salt of p-aminophenol is conducted in an atmosphere of inert gas. This is because p-aminophenol is prevented from being converted even partly into tar and thus from being colored with the tar. Similarly, use of the reducing agent is to prevent coloration of p-aminophenol by the action of dissolved oxygen in the starting solution.

The present invention will be particularly illustrated by way of the following examples in which DADPE was quantitatively determined by a gas-chromatography using a silicone-base filler. The critical value of the DADPE by the chromatographic method was found to be about 1.0 ppm.

EXAMPLE 1

130 g of crude p-aminophenol (having a purity of 96.2%, and containing 0.6% of aniline, 2.4% of DADPE, 0.6% of ammonium sulfate and 0.2% of water each on a weight basis) was dissolved in 480 g of an aqueous 10 wt % sodium hydroxide solution (which had been previously added with 3 g of anhydrous sodium dithionite) in a 2 l flask equipped with an agitator in a flow of nitrogen stream. After filtering, the filtrate was added with 100 g of aniline and agitated at 40° C. for 1 hour. Thereafter, the solution was allowed to stand, followed by separating the upper aniline layer and then adding further 100 g of aniline to effect extraction similarly. The water layer separated from the aniline layer was added with 50% sulfuric acid until the pH reached 7.2 and then cooled down to 20° C. and filtered. The resulting filter cake was washed with each 50 ml of toluene two times and then with 50 ml of an aqueous 2% acidic sodium sulfite solution, and dried in a stream of nitrogen gas to obtain 123.7 g of mearly white, pure p-aminophenol. When analyzed, this product was found to have a purity of 99.3% (i.e., a recovery percentage of 98.2%), an ash content of 0.4% and a water content of 0.2%. Neither aniline nor DADPE was detected (when analyzed by a chromatographic method, which will be used for the detection hereinlater unless otherwise indicated).

For comparison, the aqueous solution of the sodium salt of crude p-aminophenol obtained in the same manner as described above was directly neutralized to a pH of 7.2, followed by treating in the same manner as described above. The resulting p-aminophenol contained DADPE in almost the same amount as that contained in the starting crude material. Further, when the aqueous sodium salt solution was treated with active carbon without extraction with aniline, the DADPE content in the p-aminophenol was found to be 500–1000 ppm.

EXAMPLE 2

271 g (2.2 moles) of nitrobenzene, 205 g (2.05 moles) of 98% sulfuric acid, 1700 g of distilled water, 1.4 g of 5% platinum-on-carbon catalyst and 1.0 g of dodecylmethylammonium chloride were placed in a 5 l glass autoclave equipped with an agitator and subjected to a reduction reaction at 82°–86° C. under a slight pressure of hydrogen of 20–30 mHg.G. The reaction was stopped when about 9500 ml of hydrogen was absorbed.

The reaction mixture was allowed to stand for several minutes, after which the aqueous clear, upper layer was separated from the lower layer composed of unreacted nitrobenzene suspending therein the catalyst. The lower layer weighed 27 g (excluding the catalyst), which corresponded to 10% of the starting nitrobenzene. The upper layer was added with an aqueous 28% ammonia solution to adjust its pH to 5 and then with 8 g of active carbon, followed by agitating at 98°–100° C. for 5 minutes and filtering. The resulting filtrate was further added with aqueous ammonia until its pH reached 7.2 and then cooled to 10° C. in an atmosphere of nitrogen to allow p-aminophenol to precipitate. The thus precipitated p-aminophenol was separated. The crude p-aminophenol was dissolved in 880 g (2.2 moles) of an aqueous 10% sodium hydroxide solution added with 3 g of anhydrous sodium dithionite in a stream of nitrogen gas and then filtered. The resulting cake was a blackish brown tar-like material.

The filrate was charged into a 2 l flask equipped with an agitator and then added with 100 g of aniline in a stream of nitrogen. The mixture was agitated at 40° C. for 1 hour and allowed to stand, followed by removing the upper aniline layer. The lower layer of the aqueous solution of a sodium salt of p-aminophenol was neutralized with 50% sulfuric acid until its pH reached 7.2, and then cooled to 20° C. and filtered. The filter cake was washed with each 50 ml of toluene two times and then with 50 ml of an aqueous 2% acidic sodium sulfite, and dried at 60° C. in a nitrogen stream to obtain 142.6 g of almost colorless, pure p-aminophenol having a purity of 99.3%. The yield based on reacted nitrobenzene was found to be 66% (with a conversion of 88%). The pure product had an ash content of 0.3% and a water content of 0.3%, aniline, o-aminophenol, DADPE and other impurities being not detected at all.

It was found that p-aminophenol was dissolved in the crude p-aminophenol filtrate in an amount of 13.8 g, in the pure p-aminophenol filtrate in 5.2 g, and in aniline in 0.6 g. These dissolved ones were recoverable, if desired.

For comparison, the aqueous sulfuric acid solution of crude p-aminophenol obtained by the catalytic reduction of nitrobenzene was directly added with the same amount of aniline as used above without converting crude p-aminophenol into an alkali metal salt thereof in an aqueous medium. Then, the above procedure was repeated to obtain p-aminophenol. The thus obtained p-aminophenol had a DADPE content as high as 1000 ppm.

EXAMPLE 3

The aqueous sulfuric acid solution of crude p-aminophenol obtained by reducing nitrobenzene in the same manner as in Example 2 was added with an aqueous 45% sodium hydroxide solution to adjust its pH to 5.0 and then treated with active carbon as in Example 2, followed by adjusting the pH to 7.2 by the use of an aqueous 45% sodium hydroxide solution. To the solution was added 6.0 g of anhydrous sodium dithionite in a stream of nitrogen, to which was further added 195 g of an aqueous 45% sodium hydroxide solution (containing 2.2. moles of sodium hydroxide) to adjust the pH to 13. The alkaline solution was then added with 100 g of aniline, agitated at 60° C. for 1 hour, and allowed to stand. The aniline layer was separated from the solution. The above extraction procedure was repeated three times.

The aqueous solution containing the sodium salt of p-aminophenol was neutralized by addition of 50% sulfuric acid until its pH reached 7.2, cooled to 20° C., and filtered. The resulting crystals were washed with toluene and then an aqueous 2% acidic sodium sulfite solution in the same manner as in Example 2, and dried in a stream of nitrogen.

The resulting pure p-aminophenol was nearly white and had a purity of 99.1%, an ash content of 0.5% and a water content of 0.2%. Aniline, o-aminophenol, DADPE and other impurities were not detected. The pure p-aminophenol weighed 135.2 g, which corresponded to a yield of 64% based on reacted nitrobenzene (with a conversion of 88%).

Para-aminophenol was contained in the filtrate of p-aminophenol in 2.04 g and in aniline in 1.2 g.

EXAMPLE 4

Example 2 was repeated using methyl isobutyl ketone instead of aniline in the extraction procedure of impurities. The resulting pure p-aminophenol was nearly white and had a purity of 99.1%, a weight of 144.8 g, a yield of 67% (based on reacted nitrobenzene), ash and water contents of 0.6% and 0.3%, respectively. Aniline, o-aminophenol, DADPE and other impurities were not detected.

EXAMPLE 5

Example 1 was repeated using cyclohexanone instead of aniline in the extraction procedure of impurities.

The resulting pure p-aminophenol was nearly white and had a purity of 99.1%, a weight of 143 g, a yield of 66%, and ash and water contents of 0.5% and 0.3%, respectively. Aniline, o-aminophenol, DADPE and other impurities were not detected.

What is claimed is:

1. A process for the purification of crude p-aminophenol, including contacting the crude p-aminophenol with a solvent to extract impurities contained in the crude p-aminophenol, characterized by forming an aqueous alkali metal salt solution of the crude p-aminophenol in an atmosphere of an inert gas, and contacting said salt solution with an inactive organic solvent immiscible with water to permit the impurities to be separated therefrom in the inactive solvent by extraction.

2. The process according to claim 1, wherein the crude p-aminophenol is obtained by the catalytic hydrogenation of nitrobenzene in an aqueous sulfuric acid medium.

3. The process according to claim 1, wherein said salt solution forming step is conducted in the presence of a reducing agent.

4. The process according to claim 1, wherein said inactive organic solvent is an aromatic amine.

5. The process according to claim 1, wherein said alkali metal salt is sodium or potassium salt.

6. The process according to claim 3, wherein said reducing agent is anhydrous sodium dithionite and/or sodium sulfite.

7. The process according to claim 4, wherein said aromatic amine is aniline.

8. The process according to claim 2, wherein an alkali is mixed with an aqueous crude p-aminophenol solution obtained by the catalytic hydrogenation of nitrobenzene in an aqueous sulfuric acid medium to adjust the pH of the solution to 7 to 8 and to precipitate crude p-aminophenol therefrom, the resulting precipitate being separated from an aqueous phase and dissolved in an aqueous alkali metal solution, thereby to form the aqueous alkali metal salt solution of the crude p-aminophenol.

9. The process according to claim 8, wherein the concentration of said alkali in the aqueous alkali metal solution is from 5 to 15 weight %.

10. The process according to claim 8, wherein said alkali mixed with said aqueous crude p-aminophenol solution is an aqueous ammonia solution.

* * * * *